United States Patent [19]
Iwane

[11] Patent Number: 5,428,414
[45] Date of Patent: Jun. 27, 1995

[54] APPARATUS FOR MEASURING THE REFRACTIVE POWER OF AN OPTICAL SYSTEM

[75] Inventor: Toru Iwane, Yokohama, Japan

[73] Assignee: Nikon Corporation, Tokyo, Japan

[21] Appl. No.: 159,470

[22] Filed: Nov. 30, 1993

[30] Foreign Application Priority Data

Nov. 30, 1992 [JP] Japan .................. 4-320941

[51] Int. Cl.⁶ ............................................. A61B 3/10
[52] U.S. Cl. ................................. 351/214; 351/211; 356/124
[58] Field of Search ............... 351/205, 211, 214, 221; 356/124, 125, 126, 127

[56] References Cited

U.S. PATENT DOCUMENTS

| | | | |
|---|---|---|---|
| 4,199,816 | 4/1980 | Humphrey | 356/124 |
| 4,353,625 | 10/1982 | Nohda et al. | 351/211 |
| 4,526,451 | 7/1985 | Nohda | 351/211 |
| 5,148,231 | 9/1992 | Ishiguro et al. | 351/211 |
| 5,210,555 | 5/1993 | Ishikura et al. | 351/214 |

FOREIGN PATENT DOCUMENTS

0469287  2/1992  European Pat. Off. .
2951897  7/1980  Germany .
3020804  12/1980 Germany .
62-5147  1/1987  Japan .

OTHER PUBLICATIONS

*Patent Abstracts of Japan*, vol. 11, No. 173 (P-582) 4 Jun. 1987 (JP-A-62 005 147).

*Primary Examiner*—William L. Sikes
*Assistant Examiner*—Huy Mai
*Attorney, Agent, or Firm*—Shapiro and Shapiro

[57] ABSTRACT

A compact, low-cost apparatus for measuring the refractive index of an eye utilizes a chopper which forms and scans two orthogonal fringes. In a light-receiving unit, at least three light-receiving elements are arranged not to be aligned in a line. With these light-receiving elements, time differences when the fringes pass light-receiving elements in each of two pairs are measured. A control & arithmetic unit calculates the spherical power, the cylindrical power, and the cylindrical axis degree by performing predetermined calculations using the measurement data. The apparatus requires no image rotator, and hence, a compact, low-cost apparatus can be realized. Also, the measurement time can be shortened.

6 Claims, 10 Drawing Sheets

APPARATUS FOR MEASURING THE REFRACTIVE POWER OF AN OPTICAL SYSTEM

BACKGROUND OF THE INVENTION

1. Field of the Invention

The present invention relates to an apparatus used in an eye-refractometer device or an automatic lens meter and, more particularly, to an apparatus for measuring the refracting power of an optical system.

2. Related Background Art

As a method of objectively measuring the refracting power of an eye, a skiascopy is known as per, e.g., U.S. Pat. No. 4,353,625. A conventional apparatus adopting the skiascopy has a schematic structure shown in FIG. 11. The apparatus includes a projection system constituted by a light source 901, a lens 902 for collimating a light beam emitted from the light source 901, a chopper 903 for chopping the collimated light beam using a slit, and an image rotator 904 for rotating an image. An observation system is constituted by the image rotator 904 for rotating and returning light coming back from an eye to be examined (in other words, an image projected onto the fundus of the eye to be examined), and a lens 905 as a measurement optical system. A diaphragm 906 and a light-receiving unit 907 are arranged after the lens 905. The diaphragm 906 is arranged at a position conjugate with the fundus of the eye having reference refracting power, and plays a role to guide the shadow of a phase according to the refractive index of the eye to the light-receiving unit 907. The light-receiving unit 907 comprises two light-receiving elements 907$u$ and 907$d$ (FIGS. 12–14) which are vertically arranged to be separated by a predetermined interval.

The principle of measuring the refractive index by the conventional skiascopy will be described below with reference to FIGS. 12 to 14.

A fringe pattern is projected onto the fundus of an eye E to be examined by the above-mentioned projection system. The fringe pattern is moved in a predetermined direction at a predetermined speed.

When the refractive index of the eye E to be examined is normal, a fringe pattern portion formed at the same position Ea of the fringe pattern on the fundus of the eye is formed on the light-receiving elements 907$u$ and 907$d$ (see FIG. 12). Therefore, the light-receiving elements 907$u$ and 907$d$ are set in the same dark or bright state all the time. More specifically, when the light-receiving element 907$u$ is set in a bright state, the light-receiving element 907$d$ is also set in a bright state, and vice versa. In this state, an image formed on the light-receiving unit 907 simply repetitively flickers in correspondence with the dark and bright portions of fringes passing the position Ea (in this case, the fringe pattern is formed on the light-receiving unit 907, and never moves).

However, when the eye E to be examined suffers from myopia or hyperopia, an image corresponding to a position Eb is formed on the light-receiving element 907$u$, and an image corresponding to a position Ec is formed on the light-receiving element 907$d$. Therefore, the dark or bright states of the light-receiving elements 907$u$ and 907$d$ do not always coincide with each other (see FIGS. 13 and 14). Furthermore, when the fringe pattern formed on the fundus of the eye is moved (e.g., downward), the fringe pattern formed on the light-receiving unit 907 also moves in the same direction (in this case, downward; see FIG. 13) in the case of the myopia. Conversely, in the case of the hyperopia, the fringe pattern moves in the opposite direction (in this case, upward; see FIG. 14). The moving speed of the fringe pattern formed on the light-receiving unit 907 corresponds to the degree of myopia or hyperopia. Therefore, the refractive index of the eye can be measured by measuring the time after a certain fringe passes through the light-receiving element 907$u$ until it reaches the light-receiving element 907$d$ (see FIG. 15). The basic principle of the skiascopy has been described.

Upon measurement of the refracting power of an eye, however, not only the hyperopia or myopia but also astigmatism must be taken into consideration. More specifically, since the refracting power of an eye has directivity, the directivity must be taken into consideration to achieve precise measurement. For example, when an eye to be examined suffers from astigmatism, a fringe pattern formed on the fundus of the eye is rotated before it reaches the light-receiving portions, and crosses a portion between the light-receiving elements 907$u$ and 907$d$ in an oblique state, as shown in FIG. 16. Therefore, in order to obtain information about astigmatism, angles corresponding to maximum and minimum times between the light-receiving elements must be detected. For this purpose, the conventional apparatus detects the angles corresponding to the maximum and minimum times by rotating the image using the image rotator 904.

However, in the conventional apparatus, in order to obtain data associated with the refractive index (i.e., a diopter (a reciprocal number of a focal length) defined as a function of the spherical power, the cylindrical power, and the cylindrical axis degree as two-dimensional quantities), the image rotator as a means for converting scalar data into vector data must be rotated through at least half a revolution during measurement.

However, the image rotator 904 normally comprises a large prism asymmetrical about the rotational axis, and a mirror, and has a very poor balance. Therefore, to rotate the image rotator in each measurement imposes a considerable load on the structure of the apparatus. Also, it is difficult to increase the rotational speed, and this makes it difficult to reduce measurement time. In the manufacture, it is very difficult to adjust, e.g., the rotational axis of the image rotator 904. Such limitations on the structure and the manufacture increase the cost of the apparatus. In this manner, the image rotator impairs measurement precision, makes the manufacture difficult, and increases cost..

For this reason, various conventional systems without using any image rotator have been proposed. For example, as disclosed in U.S. Pat. No. 4,526,451, light beams are incident on a chopper in two orthogonal directions, and are time-divisionally extracted using these beams as horizontal and vertical scanning beams. However, in this system, the chopper must be manufactured with very high precision. In order to achieve such high precision, the chopper must be manufactured by grinding a metal, thus posing a problem of cost. In this system, two light sources must be used. However, since the light sources individually have different light amount distributions and characteristics, the variations of the light sources adversely influence the measurement values, thus disturbing high-precision measurement. For these reasons, this system is not adopted in a practical use in place of the image rotator system.

Recently, a requirement for instantaneously measuring the refracting power of an eye in, e.g., a refracting power correction operation, an intraocular lens operation, and the-like has become more common. In order to meet such a requirement, the apparatus main body must be rendered highly compact to improve mobility. However, as described above, it is difficult for the conventional apparatus to achieve a compact structure.

SUMMARY OF THE INVENTION

It is an object of the present invention to provide an apparatus for objectively measuring the refracting power of an eye, which apparatus can solve the above-mentioned problem, and can meet requirements for a compact structure, quick measurement, and low cost.

According to an aspect of the present invention, there is provided an apparatus for objectively measuring the refracting power of an eye, comprising: a light source; slit scanning means for slit-scanning light emitted from the light source in at least two directions; a projection optical system for projecting the slit-scanned light onto the fundus of an eye to be examined; a measurement optical system for extracting a shadow formed on the fundus of the eye by projecting the slit-scanned light onto the fundus of the eye; at least three light-receiving means, which are not aligned linearly, for observing movement of the shadow extracted by the measurement optical system upon slit scanning; measurement means for measuring a time required for one shadow to pass between the light-receiving means in each of two pairs thereof in units of slit-scanning directions; and arithmetic means for calculating at least one of a spherical power, a cylindrical power, and a cylindrical axis degree by solving simultaneous equations established among the spherical power, the cylindrical power, and the cylindrical axis degree the eye to be examined, the positions of the light-receiving means, the scanning directions, and the measurement result.

The slit scanning means simultaneously performs slit scans in a plurality of directions, and the arithmetic means preferably includes means for separating signals in units of slit scanning directions from the measurement result of the measurement means.

It is preferable that the slit scanning means comprise a chopper and rotation means for rotating the chopper, that chopper comprise a transmission portion for allowing light to transmit therethrough, and a light-shielding portion having a lower transmittance of light than that of the transmission portion, and that the transmission portion and the light-shielding portion have, as their boundary line, a curve given by:

$z = EXP(\tan\phi\theta + K/n\pi)$ r: distance from center of chopper
$\theta$: angular position on chopper
n: number of slits
$\phi$: angle indicating slit scanning direction
K: 0, 1, 2, ...

It is preferable that the measurement means have a function of measuring a time required for one shadow to pass by the light-receiving means (to be referred to as a "halfwave time" hereinafter), and the arithmetic means solve the simultaneous equations using a value obtained by dividing the inter-light-receiving means time by the halfwave time.

According to another aspect of the present invention, there is provided a slit member having a light-shielding portion which has, as an edge, a curve given by:

$r = EXP(\tan\phi\theta + K/n\pi)$ r: distance from center
$\theta$: angular position
n: number of slits
$\phi$: angle indicating slit scanning direction
K: 0, 1, 2, ...

According to still another aspect of the present invention, there is provided a chopper which comprises a transmission portion for allowing light to transmit therethrough, and a light-shielding portion having a lower transmittance of light than that of the transmission portion, and in which a boundary line between the transmission portion and the light-shielding portion is defined by a curve given by:

$r = EXP(\tan\phi\theta + K/n\pi)$ r: distance from center
$\theta$: angular position
n: number of slits
$\phi$: angle indicating slit scanning direction
K: 0, 1, 2, ...

In this case, it is preferable that the chopper have a substrate member, the transmission portion be constituted by the substrate member, and the light-shielding portion be formed on the surface of and/or in the substrate member.

Light emitted from the light source is slit-scanned in at least two directions by the slit scanning means. More specifically, the chopper extracts light emitted from the light source as slit light. The light is scanned by rotating the chopper by the rotation means.

The slit-scanned light is projected onto the fundus of the eye to be examined by the projection optical system., a dark or bright pattern according to the pattern of the slit, e.g., a fringe-like shadow is formed on the fundus of the eye. The measurement optical system detects the shadow on the fundus of the eye, and projects it onto the light-receiving means.

In this case, the behavior of the shadow on the light-receiving means varies depending on the refractive index of the eye to be examined in accordance with the principle of skiascopy. Although the movement of the shadow is equal to the slit-scanning frequency, the time required for one shadow to pass between each two light-receiving means changes depending on the refractive index of the eye to be examined, and the positions of the light-receiving means on a plane perpendicular to the optical axis. In this case, since the positional relationship among the light-receiving means will never move once it is determined, the time depends only on the refractive index of the eye to be examined. Therefore, the refractive index can be obtained by detecting the time between the predetermined light-receiving means, and solving the simultaneous equations established thereamong.

The measurement means measures a time required for one shadow to pass between each two light-receiving means in units of slit scanning directions. The arithmetic means separates signals in units of slit scanning directions from the measurement result of the measurement means using the separation means, and calculates at least one of the spherical power, cylindrical power, and the cylindrical axis degree. In this case, when a phase is calculated by dividing the inter-light-receiving means time by the halfwave time, the phase can be independent from the rotational speed of the chopper,, thus facilitating control.

Note that the chopper is constituted by providing a predetermined function pattern on, e.g., a disk-shaped substrate member which allows light to transmit therethrough. Therefore, when the chopper is rotated, the rotating pattern chops the light beam in accordance with the function, in other words, slit-scans the light beam.

The present invention is very effective in terms of reduction not only in cost of the apparatus but also in size of the apparatus, since the structure of the apparatus for objectively measuring the refracting power of an eye can be simplified. The measurement time can also be shortened. Such simplification of the apparatus improves mobility of the apparatus, and widens the application field of an apparatus of this type. For example, when the apparatus is rendered highly compact, it can be utilized at the site of ophthalmological operations as a member having a function of measuring the refracting power of an eye, and can also be applied to measurement of the refractive indices of bedridden patients who are not suitable for measurement in a gantry system used in the conventional apparatus, and to patients who have no will of their own such as babies, animals experimentation, and the like.

DESCRIPTION OF THE PREFERRED EMBODIMENTS

Figure 1:
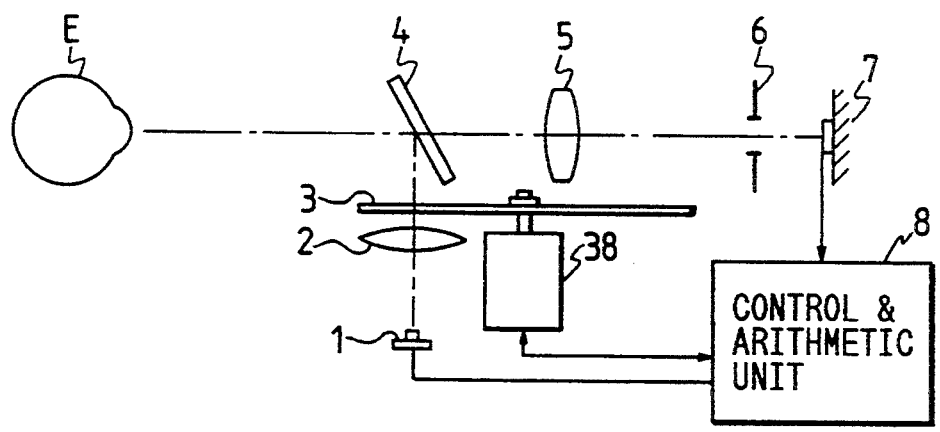
FIG. 1 is a block diagram of an apparatus for measuring refracting power according to an embodiment of the present invention.

FIG. 1 shows a schematic arrangement of an apparatus according to an embodiment of the present invention. The apparatus shown in FIG. 1 comprises a light source 1, a lens 2, a chopper 3, a half mirror 4, a lens 5, a diaphragm 6, a light-receiving unit 7, and a control & arithmetic unit 8.

The light source 1 emits light (in this embodiment, red light) required for measurement. The light source 1 of this embodiment is modulated at a frequency sufficiently higher than the scanning frequency of the chopper 3 so as to decrease the exposure amount on the fundus of an eye E to be examined. With this modulation, even when the light amount is considerably smaller than that obtained when the light source 1 is statically turned on, it can be easily electrically amplified. Of course, even when the light source 1 is statically turned on, it does not influence measurement at all.

The lens 2 collimates a light beam emitted from the light source 1. This lens 2 is basically the same as that used in the prior art.

The half mirror 4, the lens 5, and the diaphragm 6 are also basically the same as those in the prior art.

The light-receiving unit 7 will be described below.

Figure 2:
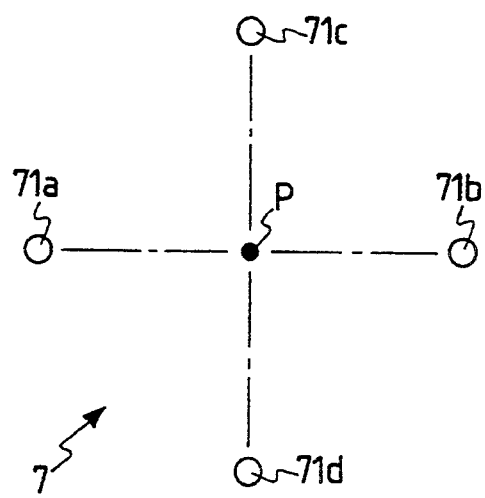
FIG. 2 is a plan view showing an arrangement of a light-receiving unit 7.

As shown in FIG. 2, the light-receiving portion of this embodiment includes four light-receiving elements (71a, 71b, 71c, and 71d). These light-receiving elements are arranged at upper, lower, right, and left positions to have a point P as the center. The distance between each two adjacent light-receiving elements 71 need only be known, but need not always be an equal distance. The light-receiving elements need not always be arranged in a so-called cross pattern, as shown in FIG. 2, but may be arranged in a T-shaped pattern. In addition, the light-receiving elements need not always be arranged at the upper, lower, right, and left positions, but may be arranged at oblique angles. In this case, however, the contents of arithmetic operations (to be described later) need be modified in correspondence with the arrangement of the light-receiving elements. Furthermore, in this embodiment, the four light-receiving elements are used. However, in practice, the cylindrical power, and the like can be calculated using three light-receiving elements which are not aligned in a line. This point will be described later.

Of course, these light-receiving elements 71 have a sufficient performance for detecting at least a change in light intensity between bright and dark portions of fringes formed by the chopper 3.

Figure 3:
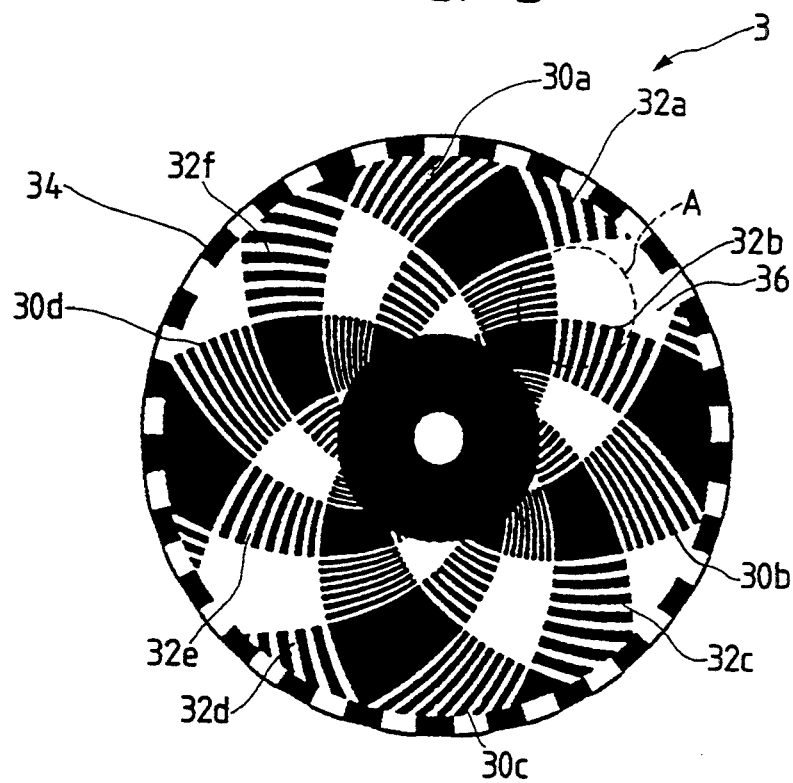
FIG. 3 is a plan view showing a chopper 3 of the embodiment shown in FIG. 1.

The chopper 3 partially shields light to form a fringe pattern, and moves (scans) the fringe pattern. In the chopper 3 of this embodiment, a disk having a light-shielding portion of a predetermined pattern is rotated by a motor 38. FIG. 3 shows a slit pattern constituting the light-shielding portion. Each of portions (30a to 30d and 32a to 32f) spirally extending from the central region of the pattern is defined by a slit for forming the dark portion of one fringe (although each slit has a fringe pattern portion and a solid black portion, they are illustrated to merely express a difference in transmittance, and the fringe pattern itself has no special meaning). The four slits 30a to 30d correspond to fringes to be scanned in the horizontal direction, and the six slits 32a to 32f correspond to fringes to be scanned in the vertical direction (the slits 30a to 30d will be referred to as "horizontal slits" hereinafter, and the slits 32a to 32f will be referred to as "vertical slits" hereinafter). In addition, a pattern 34 for detecting the rotational speed of the chopper 3 is formed on the outer peripheral edge portion of the chopper 3.

The reason why the number of horizontal slits 30 is different from the number of vertical slits 32 is to facilitate separation of signals corresponding to these scanning directions. More specifically, an apparatus which generates a certain frequency f simultaneously generates second- and fourth-order harmonics such as frequencies 2f, 4f, and the like. Therefore, when the horizontal direction is scanned at a frequency f, and the vertical direction is scanned at a frequency 2f, signals corresponding to these directions cannot be separated. For this reason, the numbers of slits in these scanning directions are preferably set to be n and n.((2K+1)/2).

The patterns of the slits will be described in detail below.

Each of the horizontal slits 30a to 30d, and the vertical slits 32a to 32f has a transmittance of 50%. A portion 36 between each two of these slits (30a to 30d and 32a to 32f) (i.e., a portion for forming a "bright portion" of the fringe pattern) has a light transmittance of about 100%. An intersecting portion between one of the horizontal slits 30a to 30d and a corresponding one of the vertical slits 32a to 32f has a transmittance of 0%. This is because two modulations (horizontal modulation and vertical modulation) are additively performed at the intersection in this embodiment. When it is preferable that modulations be multiplicatively performed, the transmittance of the overlapping portions of the two slits can be set to be 25% (in this embodiment). However, the present invention is not limited to these transmittance values. That is, a light intensity difference high enough for the above-mentioned light-receiving elements 71 to identify bright and dark portions of fringes need only be realized.

Functions adopted upon formation of the pattern are:

$$r = EXP(\theta + K/4\pi) \quad (1)$$

r: distance from center of chopper
$\theta$: angular position on chopper (with reference to upper right 45° direction in FIG. 3)
K: 0, 1, 2, ...
and
$$z = EXP(-\theta + K/6\pi) \quad (2)$$

If the pattern in a broken circle A in the upper right 45° direction in FIG. 3 is examined, it can be easily understood that a pattern scanned in the horizontal direction is equivalent to that scanned in the vertical direction. More specifically, when an eye to be examined has normal refracting power, a fringe pattern formed by the horizontal slits 30 projected onto the light-receiving unit 7 always extends in a direction substantially perpendicular to a straight line connecting the light-receiving elements 71a and 71b. Similarly, a fringe pattern formed by the vertical slits 32 always extends in a direction almost perpendicular to a straight line connecting the light-receiving elements 71c and 71d.

When the number of slits is to be increased, or when the scanning direction is changed, if the scanning direction is represented by $\phi$, and the number of slits is represented by n, slits can be formed by a pattern given by:

$$r = EXP(\tan\phi\theta + K/n\pi) \quad (3)$$

r: distance from center of chopper
$\theta$: angular position on chopper (with reference to upper right 45° direction in FIG. 3)
n: number of slits in one scanning direction
$\phi$: angle indicating slit scanning direction (with reference to upper right 45° direction in FIG. 3)
K: 0, 1, 2, ...

When the number of scanning directions is to be increased, the multiplicative type is more advantageous in terms of transmittance (at an intersection of slits) than the additive type. For example, if there are three different scanning directions, the transmittance of a portion where a single slit is solely present is set to be 50%, the transmittance of a portion where two slits overlap each other is set to be 25%, and the transmittance of a portion where three slits overlap each other is set to be 12.5%.

Note that the slit itself can be formed by a set of fine lines or a set of fine points. However, the present invention is not limited to this. That is, the slit may be formed by any other methods as long as a predetermined transmittance can be realized.

In this embodiment, the chopper 3 is realized by printing the above-mentioned slit pattern on the surface of a transparent substrate member consisting of, e.g., glass. Therefore, the chopper 3 has high precision, and can be manufactured with low cost. However, the present invention is not limited to this arrangement if slits which define a similar pattern can be realized. For example, a slit pattern may be formed inside a transparent substrate member (or between two transparent substrate members). Alternatively, a substrate member which does not allow light to transmit therethrough may be hollowed out in accordance with the above-mentioned slit pattern.

In this embodiment, the horizontal and vertical slits are formed on the single chopper 3 so as to simplify the mechanism. However, the two types of slits need not always be formed on a single chopper. For example, a chopper formed with horizontal slits and a chopper formed with vertical slits may be separately prepared, and may be arranged to overlap each other.

Furthermore, in this embodiment, since the horizontal and vertical slits are respectively arranged at equal angles, when the chopper 3 is rotated, the scanning operation can be endlessly repeated. Therefore, the chopper 3 of this embodiment can be applied, without posing any problem, to a case wherein the scanning operation need be continuously performed over a predetermined period of time due to a low processing speed of the measurement or arithmetic system.

Figure 4:
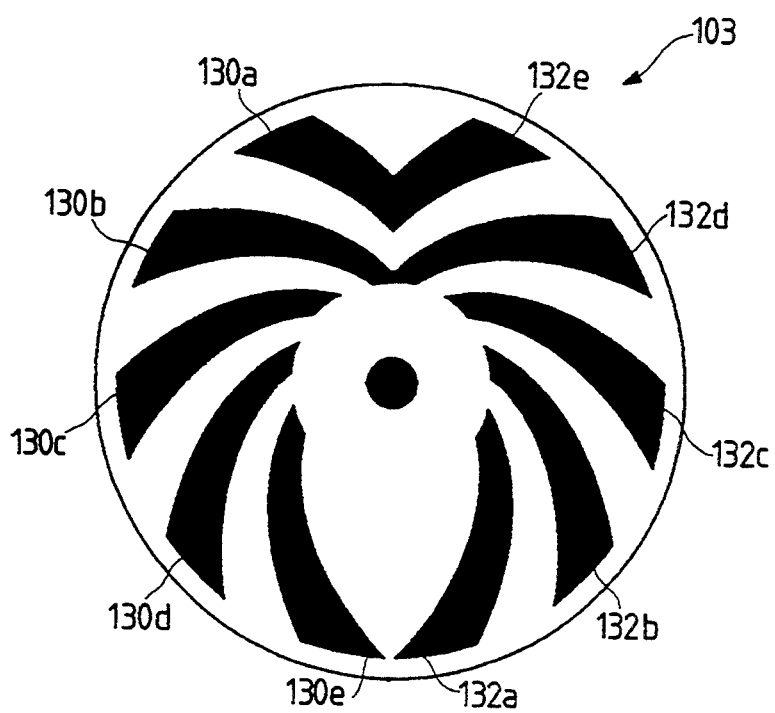
FIG. 4 is a plan view showing another chopper.

However, the present invention is not limited to this. For example, as shown in FIG. 4, horizontal slits 130a to 130e and vertical slits 132a to 132e may be formed on independent regions on a single chopper 103. In this case, since the horizontal and vertical slits are never simultaneously superposed, a signal separator 83 (to be described later) can be omitted. Also, the number of slits need not be changed in correspondence with the scanning direction.

In this embodiment, the horizontal and vertical directions are adopted as the scanning directions of the slits in correspondence with the fact that the light-receiving elements 71a to 71d (to be described later) are arranged in the horizontal and vertical directions. Therefore, when the light-receiving elements 71a to 71d are arranged in oblique directions other than the above-mentioned directions, a pattern corresponding to the arrangement of the light-receiving elements is adopted, of course. The slit pattern is determined in correspondence with the arrangement of the light-receiving elements to simplify arithmetic processing. If more complicated arithmetic processing is performed, the refractive index can be calculated even when the slit pattern does not correspond to the arrangement of the light-receiving elements.

Figure 5:
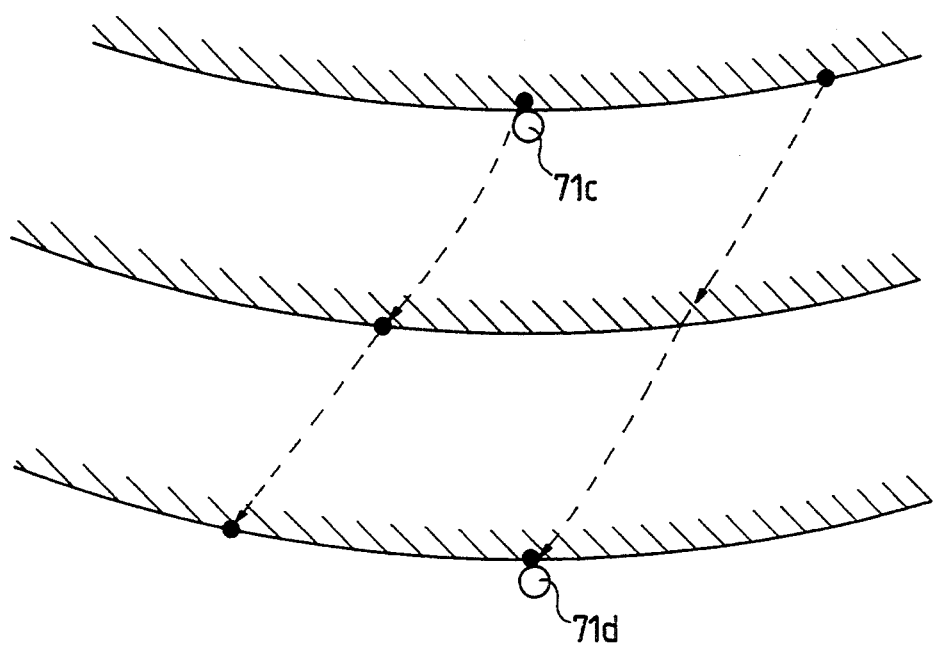
FIG. 5 is an explanatory view showing movement of a fringe pattern.

Fringes formed by the chopper 3 are not straight lines but are curves expressed by the above-mentioned equations (1), (2), and the like. The edge portion of a fringe passing through the light-receiving element 71c does not always pass through the light-receiving element 71d due to the structure of the chopper. The fringe moves while sliding in a direction perpendicular to its scanning direction (see FIG. 5). In this case, the relationship between the light-receiving elements 71c and 71d has been described, and the same applies to the relationship between the light-receiving elements 71a and 71b. For this reason, a time difference measured between two adjacent light-receiving elements includes not only components Generated by refracting power but also components generated by the fact that the fringe is a curve, and such components cause a measurement error. However, the error can be calculated and predicted in advance in design, and can be sufficiently eliminated by correcting the error in signal processing (to be described later). In order to improve measurement precision without executing such correction, measurement is performed using fringes formed by slit portions having a curvature as small as possible (i.e., slit portions present on the outer peripheral edge portion of the chopper 3), and the distance between two adjacent light-receiving elements is shortened as much as possible.

With this arrangement, when the chopper 3 of this embodiment is rotated by the motor 38, fringe patterns in a plurality of directions (the vertical and horizontal directions in this embodiment) are formed on the fundus of an eye to overlap each other, and the two directions can be simultaneously scanned. For example, when the chopper 3 is rotated at 6,000 rpm, the fringes scan the horizontal direction at 400 hz, and scan the vertical direction at 600 hz.

How do fringes formed by the above-mentioned chopper 3 behave on the light-receiving unit 7? As described above, when the refracting power is negative (i.e., in the case of hyperopia), the fringes move backward on the light-receiving elements; when the refracting power is positive (i.e., in the case of myopia), they move forward. When the refracting power is zero (i.e., in the case of a normal eye), the entire pattern flickers.

The contribution of the diopter or refractive index to a time (measurement data) required for a certain fringe to pass between two adjacent light-receiving elements will be described below. In this specification, the time will be referred to as a "phase difference" for the reason to be described later.

The phase difference is almost linear to the refractive index of an eye to be examined. Therefore, the scalar refractive index can be calculated by multiplying the phase difference with a constant.

Since the refractive index can be expressed by a 2×2 matrix of a linear transform, if it is extended to be able to be applied to this fact, the refractive index is expressed by:

$$\begin{pmatrix} phx \\ phy \end{pmatrix} = k \cdot \begin{pmatrix} s + \frac{c}{2} \cdot (1 + \cos 2\theta), & \frac{c}{2} \cdot \sin 2\theta \\ \frac{c}{2} \cdot \sin 2\theta, & s + \frac{c}{2} \cdot (1 - \cos 2\theta) \end{pmatrix} \cdot \begin{pmatrix} x \\ y \end{pmatrix} \quad (4)$$

where phx is the phase associated with scanning in the horizontal direction, and phy is the phase associated with scanning in the vertical direction, s is the spherical power, c is the cylindrical power, and $\theta$ is the cylindrical axis degree. Also, x and y are the positions of the light-receiving elements, and are determined using a point on the optical axis (i.e., the point P in FIG. 2) as the origin (0, 0). k is a constant inherent to the apparatus.

Therefore, the phases of horizontal scanning of the light-receiving elements 71a to 71d are expressed as follows when the constant part is omitted. Note that the coordinate position of the light-receiving element 71a is (1, 0), that of the light-receiving element 71b is (−1, 0), that of the light-receiving element 71c is (0, 1), and that of the light-receiving element 71d is (0, −1).

Phase of light-receiving element 71a:

$$s + c \cdot (1 + \cos 2\theta)/2 \quad (5)$$

Phase of light-receiving element 71b:

$$-s - c \cdot (1 + \cos 2\theta)/2 \quad (6)$$

Phase of light-receiving element 71c:

$$(c \cdot \sin 2\theta)/2 \quad (7)$$

Phase of light-receiving element 71d:

$$-(c \cdot \sin 2\theta)/2 \quad (8)$$

Similarly, the phases of vertical scanning are expressed as follows:

Phase of light-receiving element 71a:

$$(c \cdot \sin 2\theta)/2 \quad (9)$$

Phase of light-receiving element 71b:

$$-(c \cdot \sin 2\theta)/2 \quad (10)$$

Phase of light-receiving element 71c:

$$s + c \cdot (1 - \cos 2\theta)/2 \quad (11)$$

Phase of light-receiving element 71d:

$$-s - c \cdot (1 - \cos 2\theta)/2 \quad (12)$$

If the horizontal phase difference between the light-receiving elements 71a and 71b is represented by dx, the vertical phase difference therebetween is represented by dd2, the vertical phase difference between the light-receiving elements 71c and 71d is represented by dy, and the horizontal phase difference therebetween is represented by dd1, these phase differences are expressed as follows.

$$dx = 2 \cdot s + c \cdot (1 + \cos 2\theta) \quad (13)$$

$$dy = 2 \cdot s + c \cdot (1 - \cos 2\theta) \quad (14)$$

$$dd = dd1 = dd2 = c \cdot \sin 2\theta \quad (15)$$

Therefore, when the following equations (16) to (18) are calculated using these equations (13) to (15), the refractive index can be easily obtained.

Cylindrical power $c = \frac{1}{2} \cdot sqr(2(dx - dy) + 4dd) \quad (16)$

Spherical power $s = \frac{1}{4} \cdot (dx + dy - 2 \cdot c) \quad (17)$

Cylindrical axis degree $\theta = \tan^{-1}(2 \cdot dd/(dx-dy))$ (18)

In this manner, when the phase differences of each pair of light-receiving elements are measured, the refracting power can be calculated using the measurement results.

The control & arithmetic unit 8 will be described below.

Figure 6:
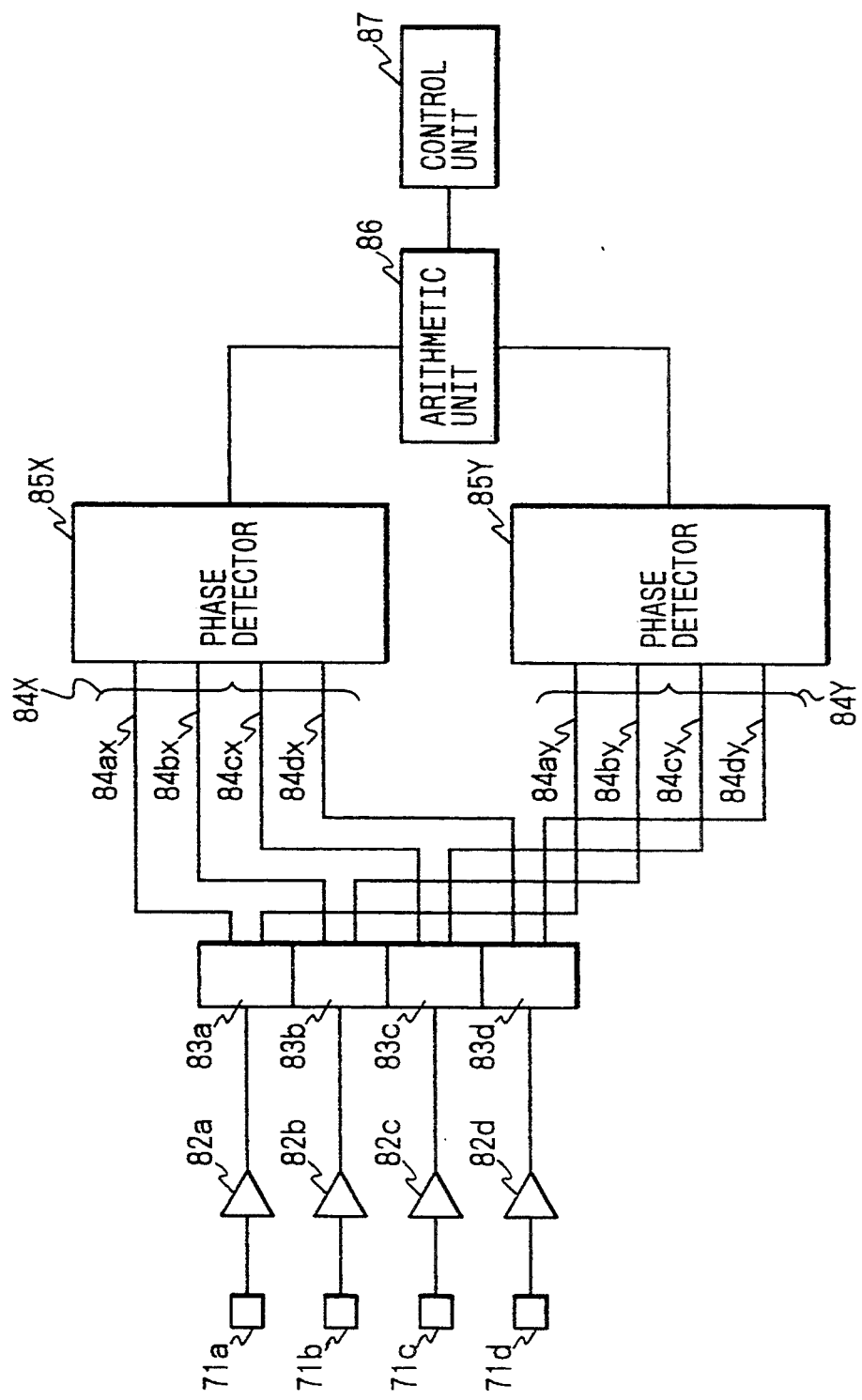
FIG. 6 is a block diagram showing an arrangement of a control & arithmetic unit.

The control & arithmetic unit 8 has a function of calculating the phases, phase differences, and refractive index by performing the above-mentioned processing for signals detected by the light-receiving unit 7. Also, the unit 8 controls and monitors the operations of the respective units such as the motor 38, the light source 1, and the like. The unit 8 includes signal amplifiers 82a to 82d, signal separators 83a to 83d, phase detectors 85X and 85Y, an arithmetic unit 86, and a control unit 87 for controlling the motor 38 and the like, as shown in FIG. 6.

The signal amplifiers 82a to 82d respectively amplify output signals from the light-receiving elements 71a to 71d.

In this embodiment, since the horizontal and vertical scanning operations are simultaneously performed, the light-receiving elements 71a to 71d output superposed signals corresponding to these scanning directions. For this reason, these signals must be separated in units of components. The signal separators 83a to 83d have a function of electrically separating the signal components in units of scanning directions. The signal separators 83a to 83d output phase signals 84ax to 84dx associated with horizontal scanning to the phase detector 85X, and outputs phase signals 84ay to 84dy associated with vertical scanning to the phase detector 85Y. The present invention is not particularly limited with respect to the detailed arrangement of the signal separators 83a to 83d. For example, the signal separators 83a to 83d may comprise filters or tuning amplifiers.

Note that the phase of the phase signal 84ax is expressed by the above-mentioned equation (5), and the phase of the phase signal 84bx is expressed by the above-mentioned equation (6). Similarly, the phases of the phase signals 84cx and 84dx are respectively expressed by equations (7) and (8). The phases of the phase signals 84ay to 84dy are respectively expressed by equations (9) to (12).

The phase differences can be measured by detecting time differences between the leading edges of the signals after these signals are sufficiently amplified and wave-shaped. For example, the horizontal phase difference between the light-receiving elements 71a and 71b can be considered as a signal delay from the leading edge of the phase signal 84ax to that of the phase signal 84bx. When these two timings are measured by, e.g., a counter, a value representing the phase difference can be obtained.

Figure 7A:
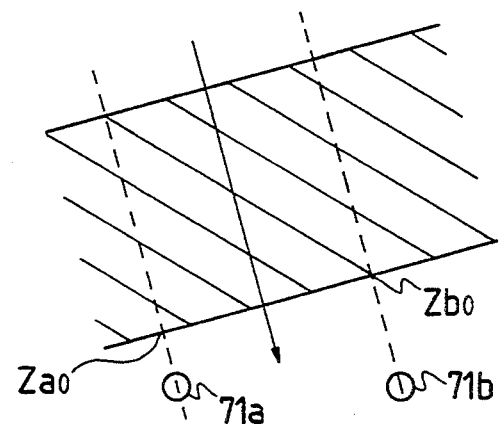
FIGS. 7A and 7B are explanatory views showing the relationship between the rotational direction of a fringe pattern and light-receiving elements.
Figure 7B:
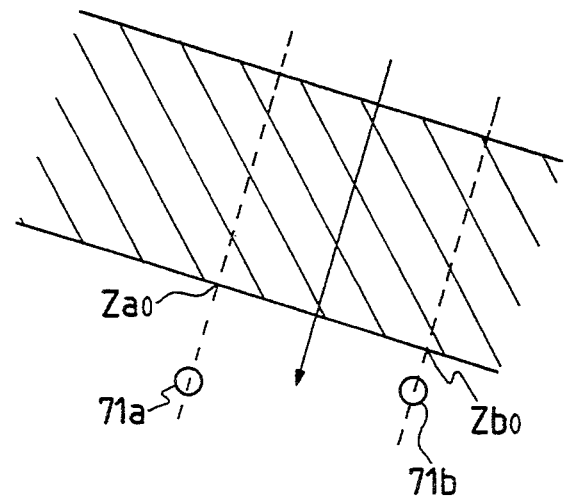

However, it is not preferable in terms of an actual circuit arrangement and signal processing to directly measure the signal delay ($\Delta t0$) since the rotational direction of fringes projected onto the light-receiving unit 7 varies depending on the content of an astigmatism component of an eye. As a result, the sign of the measurement value ($\Delta t0$) is reversed between the rotational directions of the fringes shown in, e.g., FIGS. 7A and 7B. Also, when the time difference is small, measurement may be disabled. Note that the signal delay $\Delta t0$ has a meaning expressed by equation (19) below in association with FIGS. 7A and 7B:

$$\Delta t0 = Tz_{a0} - Tz_{b0} \quad (19)$$

where $Tz_{a0}$ is the time at which the light-receiving element 71a detects the leading edge of a signal by an edge portion $Z_{a0}$ of a fringe, and $Tz_{b0}$ is the time at which the light-receiving element 71b detects the leading edge of a signal by an edge portion $Z_{b0}$ of a fringe.

Figure 8:
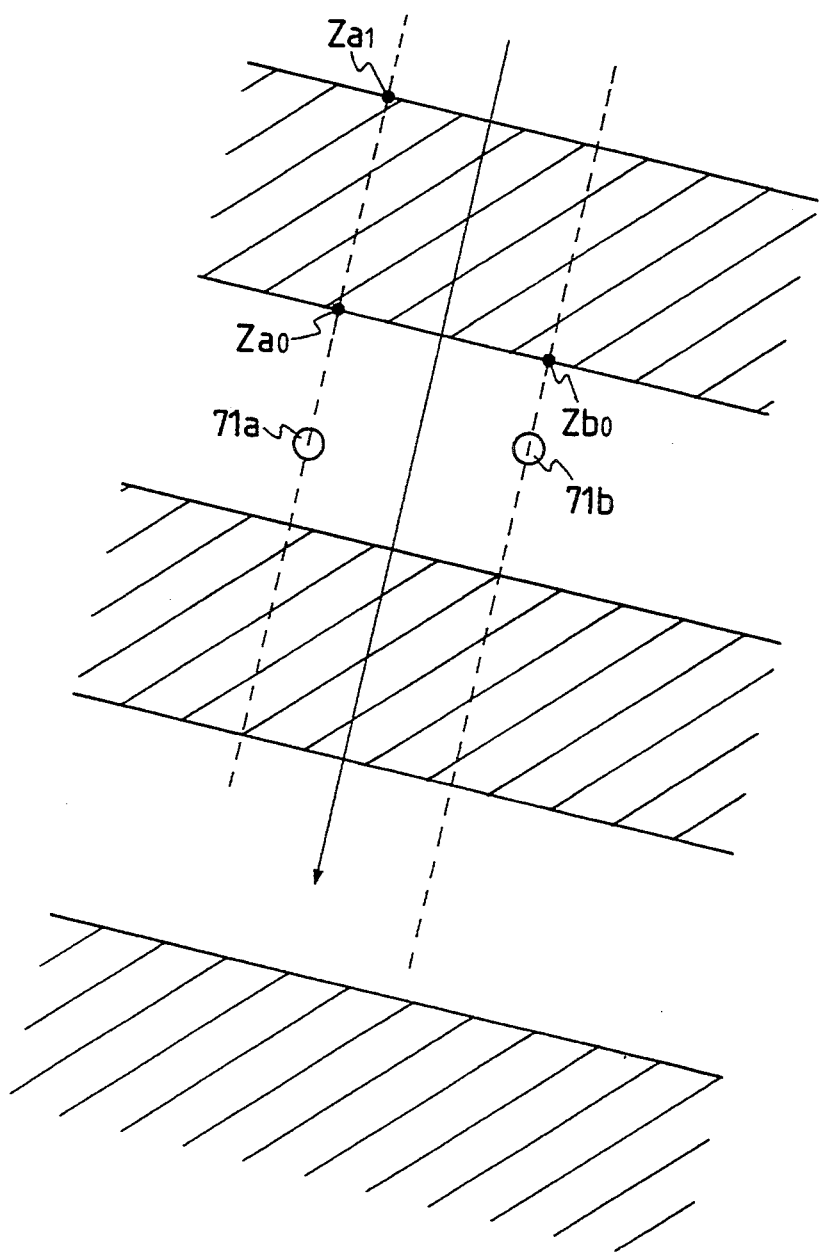
FIG. 8 is an explanatory view showing the relationship between a fringe pattern and the light-receiving elements.

For this reason, in this embodiment, a time difference ($\Delta t0 + \Delta t\pi$) between the time $Tz_{b0}$ at which the light-receiving element 71b detects the edge portion $Z_{b0}$ of a fringe in FIG. 8, and time $Tz_{a1}$ at which the light-receiving portion 71a detects an edge portion $Z_{a1}$ is measured. Also, a time difference ($\Delta t0$) between the times $Tz_{a0}$ and $Tz_{a1}$ is measured. The sign of the measurement value ($\Delta t0 + \Delta t\pi$) measured in this manner will never be reversed depending on the rotational direction of fringes, and it is convenient in the use of a counter. When another time difference is divided by a time ($\Delta t\pi$) corresponding to a halfwave $\pi$ in actual measurement, a true phase difference from which factors such as the manufacturing error of the chopper 3, a variation in rotation of the motor 38, and the like are eliminated can be measured. In this sense, in this specification, the time difference between each two light-receiving elements 71 has been referred to as the "phase difference".

Figure 9:
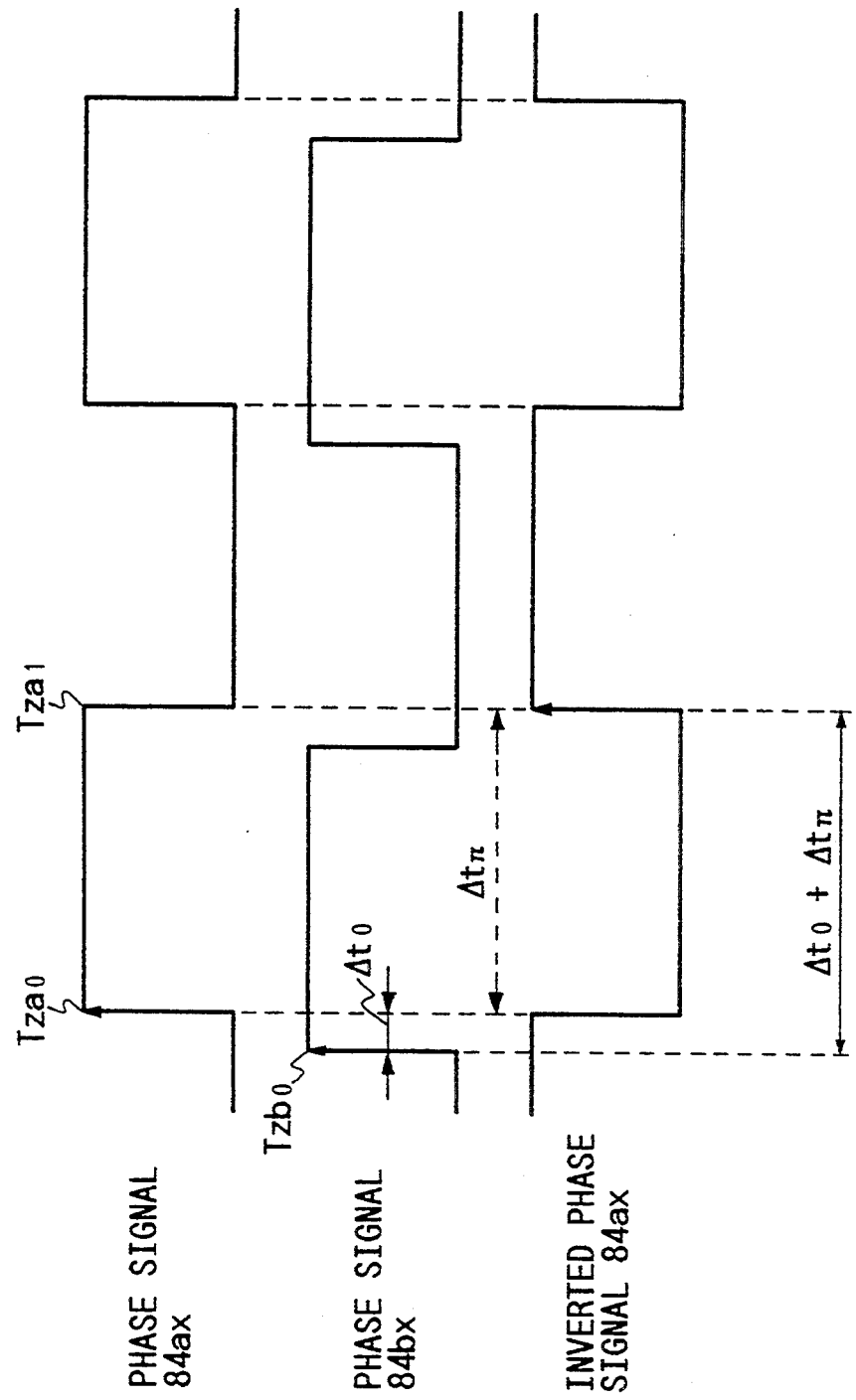
FIG. 9 is a timing chart for explaining a detection signal of a light-receiving element 71.

In practice, as shown in FIG. 9, measurement is realized by measuring a time difference between the leading edges of a signal obtained by inverting the phase signal 84ax and the phase signal 84bx. In this case, the measurement of the time difference between the phase signals 84ax and 84bx has been described. Similarly, the same applies to signal processing of other light-receiving elements..

When this measurement value is used, the above-mentioned variables (equations (13) to (15)) can be expressed as follows:

$$dx = a(\tau x!ab - \tau x!aa)/\tau x!aa \quad (20)$$

$$dy = a(\tau x!ad - \tau y!ac - \tau y!aa)/\tau y!aa \quad (21)$$

$$dd1 = a(\tau x!ad - \tau x!ac - \tau x!aa)/\tau x!aa \quad (22)$$

$$dd2 = a(\tau y!ab - \tau y!aa)/\tau y!aa \quad (23)$$

where $a$ is a constant inherent to the apparatus, a represents the phase signal 84ax or 84ay, and b represents the phase signal 84bx or 84by. The same applies to c and d. Also, ! a represents a signal obtained by inverting a. $\tau x!ab$ represents the time difference between the inverted signal of the phase signal 84ax and the phase signal 84bx. $\tau x!aa$ represents the time difference between the inverted signal of the phase signal 84ax and the phase signal 84ax (i.e., the time ($\Delta t\pi$) corresponding to the halfwave $\pi$). Similarly, $\tau y!ad$ represents the time difference between the inverted signal of the phase signal 84ay and the phase signal 84dy. $\tau y!aa$ represents the time difference between the inverted signal of the phase signal 84ay and the phase signal 84ay (i.e., the time ($\Delta t\pi$) corresponding to the halfwave $\pi$).

In this case, !a is used as a reference, and all time differences are defined and measured in association with only !a. Therefore, ($\tau y!ad - \tau y!ac$) in equation (21) corresponds to the time difference (i.e., $\tau y!dc$ or $\tau y!cd$) between the phase signals 84cy and 84dy. Similarly, ($\tau$x!ad−$\tau$x!ac) in equation (22) corresponds to the time difference (i.e., $\tau$x!dc or $\tau$x!cd) between the phase signals 84cx and 84dx.

When the above-mentioned equations (16) to (18) are calculated using these variables (equations (20) to (23)) obtained in this manner, the refracting power of an eye to be examined can be calculated. These calculations are executed by the arithmetic unit 86 and the like.

Finally, data required in calculations of refracting power according to the method of the present invention will be described below.

Time T(tx1, ty1) at which a light receiving element arranged at a position X1(x1, y1) detects a signal is given by:

$$T = D \cdot \Phi \cdot X_1 \tag{24}$$

D in equation (24) is the matrix given by:

$$D = \begin{pmatrix} s + \frac{c}{2}(1 + \cos2\theta) & \frac{c}{2} \cdot \sin2\theta \\ \frac{c}{2} \cdot \sin2\theta & s + \frac{c}{2}(1 - \cos2\theta) \end{pmatrix} \tag{25}$$

$\phi$ in equation (24) represents the rotation of an angle $\phi$ given by:

$$\Phi: \begin{pmatrix} \cos\phi & \sin\phi \\ -\sin\phi & \cos\phi \end{pmatrix} \tag{26}$$

$X_1$ in equation (24) represents the position of the light-receiving element, and is given by:

$$X_1 = \begin{pmatrix} x_1 \\ y_1 \end{pmatrix} \tag{27}$$

T in equation (24) represents the detection time of a signal, and is given by:

$$T = \begin{pmatrix} tx_1 \\ tx_2 \end{pmatrix} \tag{28}$$

Assuming a case wherein the two scanning directions extend perpendicular to each other, i.e., a case wherein $\phi=0$, equation (26) is rewritten as:

$$\Phi = \begin{pmatrix} 1 & 0 \\ 0 & 1 \end{pmatrix} \tag{29}$$

Therefore, equation (24) is rewritten as:

$$\begin{pmatrix} tx_1 \\ ty_1 \end{pmatrix} = \begin{pmatrix} s + \frac{c}{2}(1 + \cos2\theta) & \frac{c}{2} \cdot \sin2\theta \\ \frac{c}{2} \cdot \sin2\theta & s + \frac{c}{2}(1 - \cos2\theta) \end{pmatrix} \begin{pmatrix} x_1 \\ y_1 \end{pmatrix} + \begin{pmatrix} Px \\ Py \end{pmatrix} \tag{30}$$

Equation (30) includes two orthogonal scanning components in advance, the horizontal scanning time (phase) is represented by $tx_1$, and the vertical scanning time (phase) is represented by $ty_1$.

When only the horizontal scanning component in equation (30) is considered, we have:

$$tx_1 = x_1 \cdot \left(s + \frac{c}{2}(1 + \cos2\theta)\right) + y_1 \cdot \frac{c}{2}\sin2\theta + Px \tag{31}$$

When the second light-receiving element present at a position X2(x2, y2) is considered, we have:

$$tx_2 = x_2 \cdot \left(s + \frac{c}{2}(1 + \cos2\theta)\right) + y_2 \cdot \frac{c}{2} \cdot \sin2\theta + Px \tag{32}$$

When Px is eliminated from equations (31) and (32), we have:

$$t' = x' \left(s + \frac{c}{2}(1 + \cos2\theta)\right) + y' \cdot \frac{c}{2} \cdot \sin2\theta \tag{33}$$

for x′=x1−x2, y′=y1−y2, and t′=tx1−tx2.

Assuming that the third light-receiving element is present, another equation from which Px is eliminated can be obtained as in equation (33). In other words, two equations can be obtained for horizontal scanning. In this case, the third light-receiving element must not be located on the same line as the first and second light-receiving elements. If the third light-receiving element is present on the same line, an equation to be obtained becomes substantially the same as equation (33).

As for vertical scanning, two equations can be similarly obtained.

Since four equations are obtained for three unknowns (s, c, $\theta$), if these equations are simultaneously calculated, the unknowns can be calculated.

Next, assume that the scanning directions do not extend perpendicular to each other, i.e., $\phi=\phi1$ and $\phi2$ (for $\phi1\neq0$ and $\phi2\neq0$) in equation (28).

In this case, equation (28) is rewritten as equations (34) and (35) below:

$$\begin{pmatrix} tx_1 \\ ty_1 \end{pmatrix} = \begin{pmatrix} s + \frac{c}{2}(1 + \cos2\theta) & \frac{c}{2} \cdot \sin2\theta \\ \frac{c}{2} \cdot \sin2\theta & s + \frac{c}{2}(1 - \cos2\theta) \end{pmatrix} \begin{pmatrix} \cos\phi_1 & \sin\phi_1 \\ -\sin\phi_1 & \cos\phi_1 \end{pmatrix} \begin{pmatrix} x_1 \\ y_1 \end{pmatrix} + \begin{pmatrix} Px \\ Py \end{pmatrix} \tag{34}$$

$$\begin{pmatrix} tx_2 \\ ty_2 \end{pmatrix} = \begin{pmatrix} s + \frac{c}{2}(1 + \cos2\theta) & \frac{c}{2} \cdot \sin2\theta \\ \frac{c}{2} \cdot \sin2\theta & s + \frac{c}{2}(1 - \cos2\theta) \end{pmatrix} \begin{pmatrix} \cos\phi_2 & \sin\phi_2 \\ -\sin\phi_2 & \cos\phi_2 \end{pmatrix} \begin{pmatrix} x_2 \\ y_2 \end{pmatrix} + \begin{pmatrix} Px \\ Py \end{pmatrix} \tag{35}$$

When the calculations are performed using these equations, the unknowns can be obtained.

Figure 10A:
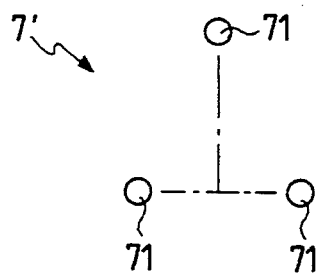
FIGS. 10A and 10B are explanatory views showing an arrangement used when three light-receiving elements are used.
Figure 10B:
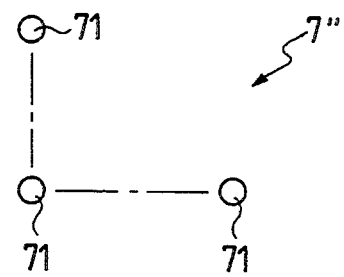
Figure 11:
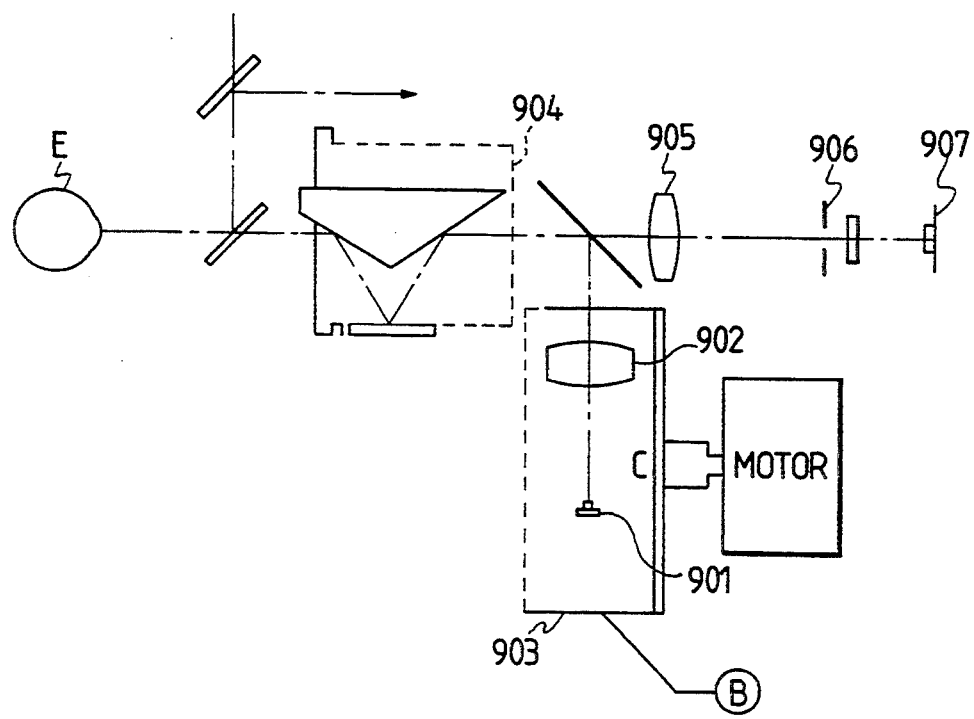
FIG. 11 is an explanatory view showing a conventional apparatus.
Figure 12:
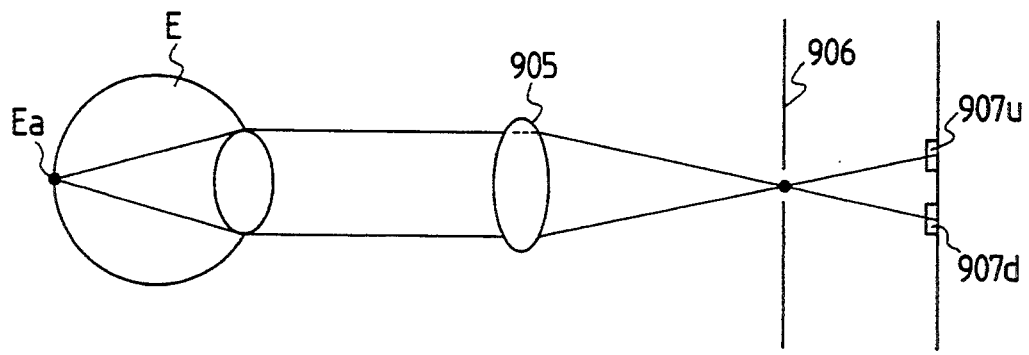
FIG. 12 is an explanatory view showing a state wherein the skiascopy is applied to an eye having normal refractive index.
Figure 13:
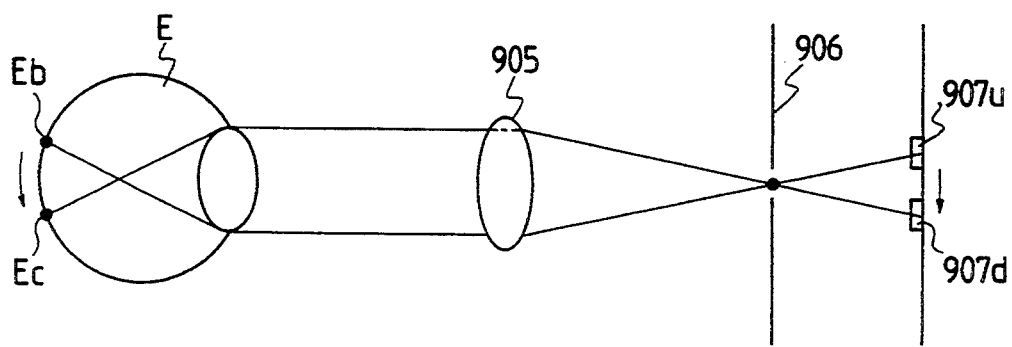
FIG. 13 is an explanatory view showing a state wherein the skiascopy is applied to an eye suffering from myopia.
Figure 14:
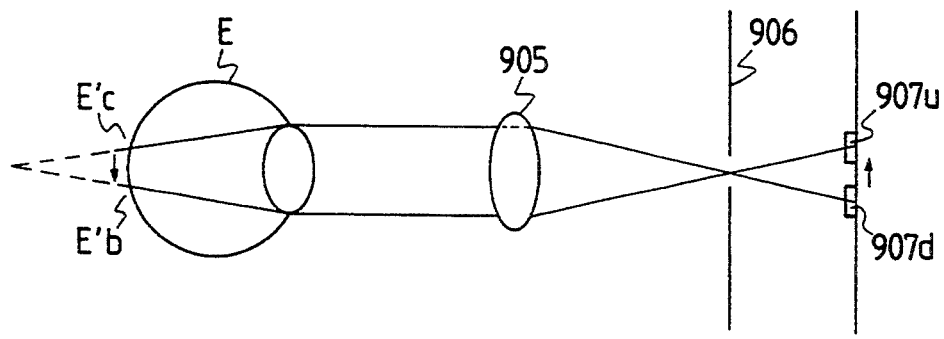
FIG. 14 is an explanatory view showing a state wherein the skiascopy is applied to an eye suffering from hyperopia.
Figure 16:
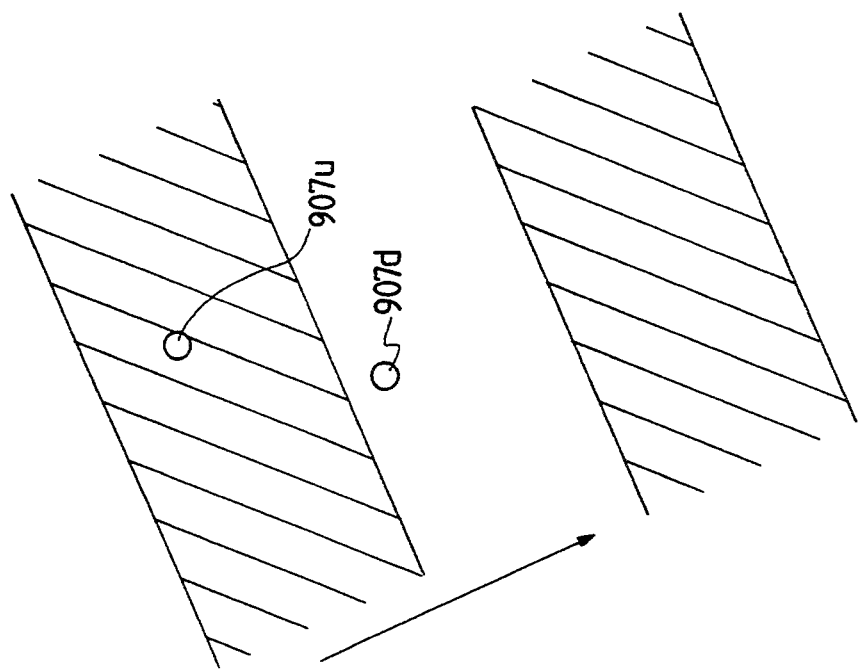
FIG. 16 is an explanatory view showing a scanning state of a fringe pattern when an eye to be examined suffers from astigmatism.
Figure 15:
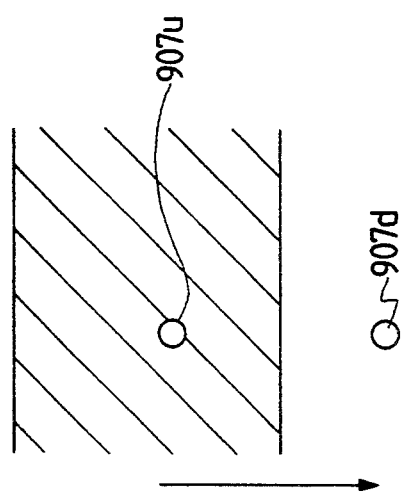
FIG. 15 is an explanatory view showing a scanning state of a fringe pattern when an eye to be examined does not suffer from astigmatism.

In this embodiment, the four light-receiving elements are arranged. As described above, if there are at least two scanning directions and three light-receiving elements which are not arranged on a single line, the spherical power, the cylindrical power, and the cylindrical axis degree can be obtained. Therefore, the light-receiving elements 71 in the light-receiving unit may be arranged, as shown in FIGS. 10A and 10B.

As described above, according to the above embodiment, no image rotator is required, and the apparatus can be rendered compact. Since the scanning operations in a plurality of directions can be simultaneously performed, a time required for examination can be shortened. Since phases are used in calculations, no precise control of the motor is required, and limitations on control can be eliminated. Also, the chopper can be manufactured with high precision. Therefore, the cost of the apparatus can be reduced.

What is claimed is:

1. An apparatus for measuring refractive power of an optical system, comprising:

means for simultaneously scanning the optical system with first light at a first scanning frequency $f_1$ in a first direction crossing an optical axis of the optical system and with second light at a second scanning frequency $f_2$ in a second direction crossing said optical axis and differing from said first direction, such that the first and second light are superimposed on each other on the optical system;

light receiving means including at least three light receiving elements arranged so as not to be in line, the respective light receiving elements receiving the first light and second light from the optical system and producing output signals;

signal separating means for separating each of the output signals from said light receiving elements into a signal component of said first scanning frequency $f_1$ and a signal component of said second scanning frequency $f_2$; and arithmetic means for calculating a refractive power of said optical system, based on a phase difference of separated signal components from a first pair of said light receiving elements and a phase difference of separated signal components of a second pair of said light receiving elements.

2. An apparatus according to claim 1, wherein said scanning means includes:

a light source;

means for slit-scanning light from said light source in two directions; and projection optical means for projecting the slit-scanned light onto said optical system.

3. An apparatus according to claim 1, wherein said slit-scanning means includes a disk-shaped rotary chopper which is arranged to cross an optical path between said light source and said optical system;

said chopper has a first group of slits which are disposed in an area surrounding a center of rotation of said chopper and formed to cross said optical path in a direction corresponding to said first direction upon rotation of said chopper, and a second group of slits which are disposed in said area and superimposed on said first slits and which are formed to cross said optical path in a direction corresponding to said second direction upon rotation of said chopper; and the number of first slits is different from the number of second slits.

4. An apparatus according to claim 3, wherein said first group of slits includes n slits arranged substantially uniformly in a peripheral direction of said chopper, and said second group of slits includes $n \cdot ((2K+1)/2)$ slits arranged substantially uniformly in the peripheral direction.

5. An apparatus according to claim 3, wherein each of said first and second groups of slits has a light transmission portion and a light-shielding portion having a transmittance lower than a transmittance of said light transmission portion, and said light transmission portion and said light shielding portion have a boundary line extending along a curve given by:

$r = EXP(\tan\phi\theta + K/n\pi)$ where r: the distance from the center of rotation of said chopper;

$\theta$: the rotational angular position on said chopper;

n: the number of said light transmission portions;

$\phi$: the angle indicating the slit scanning direction; and

K: 0, 1, 2, ...

6. An apparatus according to claim 1, wherein said arithmetic means calculates at least one of a spherical power, a cylindrical power, and a cylindrical axis degree by solving simultaneous equations established among the spherical power, the cylindrical power, and the cylindrical axis degree of said optical system, positions of said light-receiving elements, said first and second scanning directions, and said phase differences.

* * * * *